(12) United States Patent
Macheras

(10) Patent No.: US 8,435,982 B2
(45) Date of Patent: May 7, 2013

(54) PHARMACEUTICAL FORMULATION CONTAINING LIPOPHILIC DRUGS AND MILK AS A SOLUBILIZING/DISPENSING AGENT AND METHOD FOR THE PREPARATION THEREOF

(75) Inventor: Panayotis Macheras, Athens (GR)

(73) Assignee: Pharmathen S.A., Pallini, Attikis (GR)

( * ) Notice: Subject to any disclaimer, the term of this patent is extended or adjusted under 35 U.S.C. 154(b) by 289 days.

(21) Appl. No.: 12/743,428

(22) PCT Filed: Nov. 28, 2008

(86) PCT No.: PCT/EP2008/010118
§ 371 (c)(1),
(2), (4) Date: May 18, 2010

(87) PCT Pub. No.: WO2009/068301
PCT Pub. Date: Jun. 4, 2009

(65) Prior Publication Data
US 2010/0267705 A1    Oct. 21, 2010

Related U.S. Application Data

(60) Provisional application No. 61/004,693, filed on Nov. 30, 2007.

(51) Int. Cl.
*A61K 31/5415*    (2006.01)
*A61K 31/196*    (2006.01)

(52) U.S. Cl.
USPC ...................... 514/226.5; 514/567

(58) Field of Classification Search .................. None
See application file for complete search history.

(56) References Cited

U.S. PATENT DOCUMENTS

| 4,003,989 A | 1/1977 | Bar-On | |
|---|---|---|---|
| 2002/0169212 A1 * | 11/2002 | Stroble et al. | 514/570 |
| 2004/0254243 A1 * | 12/2004 | Beguer et al. | 514/554 |

FOREIGN PATENT DOCUMENTS

| GB | 932378 A | 7/1963 |
|---|---|---|
| GB | 1235540 A | 6/1971 |

OTHER PUBLICATIONS

Mishra Dina Nath et al: "Investigations on analgesic, anti-inflammatory and ulcerogenic potential of meloxicam solid dispersion prepared with skimmed milk" Yakugaku Zasshi, vol. 126, No. 7, Jul. 2006, pp. 495-498.

Topaloglu Yalcin et al: "Inclusion of ketoprofen with skimmed milk by freeze-drying" FARMACO (Lausanne), vol. 54, No. 10, Oct. 30, 1999, pp. 648,652.

Sahin Nefise Ozlen et al: "Inclusion Complex of Prednisolone with Skimmed Milk, Part I: Physiochemical Characterization" Yakugaku Zasshi, vol. 127, No. 8, Apr. 15, 2007, pp. 1255-1261.

Topaloglu Yalcin et al: "Modulation of Anti-inflammatory Drugs' Ulcerogenicity Via Solid Dispersion with Skimmed Milk on the Example Indomethacin" ACTA Pharmaceutica Turcica, vol. XXXIX, No. 4, 1997, pp. 167-170ci.

Gonullu Omit et al: "Modulation of Anti-inflammatory Drugs' Ulcerogenicity Via Solid Dispersion with Skimmed Milk on the Example Ketoprofen" ACTA Pharmaceutica Turcica, vol. XLIII, No. 3,4, 2001, pp. 169-172.

* cited by examiner

*Primary Examiner* — Blessing Fubara
*Assistant Examiner* — Jennifer Berrios
(74) *Attorney, Agent, or Firm* — AKC Patents LLC; Aliki K. Collins

(57) ABSTRACT

The present invention relates to an improved pharmaceutical composition and in particular to a pharmaceutical formulation for oral administration comprising a therapeutically effective quantity of a lipophilic active ingredient with milk as a solubilizing/dispersing agent and methods for the preparation thereof.

13 Claims, 5 Drawing Sheets

PHARMACEUTICAL FORMULATION CONTAINING LIPOPHILIC DRUGS AND MILK AS A SOLUBILIZING/DISPENSING AGENT AND METHOD FOR THE PREPARATION THEREOF

TECHNICAL FIELD OF THE INVENTION

The present invention relates to pharmaceutical compositions for oral administration with enhanced absorbability comprising a therapeutically effective quantity of insoluble or practically insoluble in water lipophilic active ingredient or a pharmaceutically acceptable salt thereof, in conjunction with milk as a solubilizing/dispersing agent and a method for the preparation thereof.

BACKGROUND OF THE INVENTION

It is already known that the aqueous solubility of an active ingredient is a key parameter which governs its oral bioavailability. Lipophilic active ingredients and their pharmaceutically acceptable salts and derivatives are insoluble or practically insoluble in water and that results to low bioavailability of the active ingredient. Said lipophilic drugs have many disadvantages related to the fact that they are poorly absorbed from the gastrointestinal tract. Therefore, the improvement of the rate and extent of absorption of lipophilic drugs is highly desirable.

Moreover, drugs with low solubility in water (by which is meant having a solubility of less than 0.1 percent by weight in water at 20° C.) cause additional formulation problems due to their poor rate and extent of dissolution in aqueous media, including gastrointestinal fluids, which results in low absorption into systemic circulation after oral ingestion.

Various methods are already known to facilitate adequate absorption from the gastrointestinal tract and to increase the dissolution rate of oral dosage forms comprising a lipophilic active ingredient or salts and derivatives thereof. However, the prior art has encountered substantial difficulties in the production of the oral solid formulations of a desirable bioavailability.

In order to make a composition containing such a drug that will enable maximum absorption from the gastrointestinal tract, it is known to modify the crystalline structure of the active ingredient via micronization, spray drying or freeze drying or to modify the non-polarity of the active ingredient by alteration of the media in which the drug is dissolved.

However, the modification of the structure of the crystals can still not enable full dissolution and absorption of the active ingredient and unless said crystal modification is carefully controlled to be the same in every batch of the dosage form, release characteristics may vary from batch to batch.

Further, the modification of the media can be achieved by either adjusting the pH and/or the use of solubilizing agents, such as co-solvents, surfactants, complexing agents and oil/lipids.

However, the effect of such methods is not always satisfactory. For example, liquid lipid-based formulations need to be filled into soft gelatin capsules. This is not only an economical drawback but also raises capsule compatibility issues. Besides, some of the solubilizing agents are used in great quantities which might produce undesired side effects. Overall, these approaches are limited in the range and quantity of drugs which they can accommodate and also in their ability to promote the access of drug throughout the gastrointestinal wall.

Synthetic emulsions have also been used for oral administration of sparingly soluble drugs e.g. cyclosporine is formulated as a microemulsion. U.S. Pat. No. 5,447,961 discloses an oil-in-water type of emulsion containing milk for cosmetic purposes and U.S. Pat. No. 4,994,496 discloses the use of milk globules as carriers for drugs.

In addition, several documents denote the research on the solubility of lipophilic drugs in milk. The rate of dissolution of commercial formulations of lipophilic drugs in milk was found to be lower than the corresponding one in aqueous media. In another report, the rate of dissolution of lipophilic drugs used in a powder form was much higher in milk than in aqueous media. A series of in vitro and in vivo studies with reconstituted freeze-dried drug-milk formulations have demonstrated their superiority in regard to solubility and dissolution as well as the absorbability when compared to conventional capsule formulations of lipophilic drugs. Furthermore, it is known that food enhances the extent of absorption of lipophilic drugs.

Further, it is well known that a large number of drugs such as non-steroidal anti inflammatory drugs (NSAIDs) when taken orally in various dosage forms such as tablets, capsules, caplets, as well as chewable forms, create stomach irritation.

Although each of the above documents represents an attempt to overcome the problem of solubility of lipophilic drugs, there still exists a need for improving the bioavailability of a pharmaceutical composition containing a lipophilic active ingredient with milk as a solubilizing/dispersing agent.

SUMMARY OF THE INVENTION

It is, therefore, an object of the present invention to provide an improved pharmaceutical composition for oral administration containing a therapeutically effective quantity of insoluble or practically insoluble in water lipophilic active ingredient or a pharmaceutically acceptable salt or derivative thereof, which overcomes the deficiencies of the prior art and enhances the bioavailability of the active ingredient.

Another aspect of the present invention is to provide a dosage formulation for oral administration containing an insoluble or practically insoluble in water lipophilic active ingredient or a pharmaceutically acceptable salt thereof, which is bioavailable, effective, with sufficient self-life, good pharmacotechnical properties enhancing patient compliance and reducing possible side effects and gastrointestinal disorders to patients.

A further aspect of the present invention is to provide a method for the preparation of a dosage formulation for oral administration containing a therapeutically effective quantity of insoluble or practically insoluble in water lipophilic active ingredient or a pharmaceutically acceptable salt or derivative thereof, thereby enhancing the bioavailability of the active ingredient, improving the pharmacotechnical characteristics of the composition and being cost effective.

In accordance with the above objects of the present invention, a pharmaceutical composition for oral administration is provided comprising a therapeutically effective quantity of insoluble or practically insoluble in water lipophilic active ingredient or a pharmaceutically acceptable salt or derivative thereof, and an effective amount of milk as a solubilizing/dispersing agent to enhance bioavailability and/or improve solubility, wherein a solution of said active ingredient and a buffer or alcoholic solution is formed and an appropriate volume of said solution containing the therapeutic dose of the active ingredient is dispersed to a volume of milk between 20 and 500 mL and subsequently it is being gentle agitated prior to oral administration.

Thus, according to the present invention a pharmaceutical composition is prepared, in order to present the lipophilic drug in a dissolved form in the gastrointestinal tract using milk as a dispersing medium, which is a natural, abundant and inexpensive carrier with the desired characteristics for oral drug delivery.

According to another embodiment of the present invention, a process for the preparation of a pharmaceutical composition for oral administration comprising a therapeutically effective quantity of insoluble or practically insoluble in water lipophilic active ingredient or a pharmaceutically acceptable salt and derivative thereof, and an effective amount of milk as a solubilizing/dispersing agent to enhance bioavailability and/or improve solubility is provided, which comprises:
- forming a solution of the total quantity of said active ingredient with a buffer or alcoholic solution;
- dispersing the formed solution to a volume of milk between 20 and 500 ml and subsequently gentle agitating prior to oral administration.

Another aspect of the present invention is the use of a pharmaceutical composition comprising a lipophilic active ingredient dissolved in a suitable buffer or alcoholic solution for the preparation of a drug-milk solution, wherein an appropriate volume of said solution is added to a certain volume of milk during its manufacture in order to obtain the finally packaged drug-milk solution containing multiples doses of the drug.

Further preferred embodiments of the present invention are defined in the dependent claims.

Other objects and advantages of the present invention will become apparent to those skilled in the art in view of the following detailed description.

DETAILED DESCRIPTION OF THE INVENTION

Figure 1:
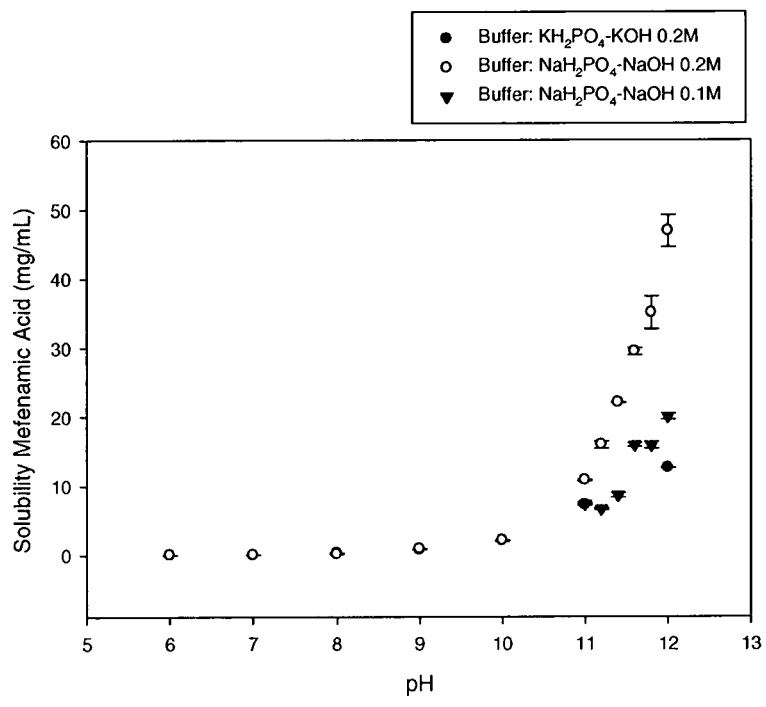
FIG. 1 shows solubility of Mefenamic acid in different buffers and pH values of each buffer according to the present invention.

For the purposes of the present invention, an insoluble or practically insoluble in water lipophilic active ingredient contained in a dosage form is considered to be an active ingredient of Class II of the Biopharmaceutics Classification System (BSC). According to the BCS, drug substances are classified as follows:

TABLE 1

Biopharmaceutics Classification System (BSC)

| CLASS | PERMEABILITY | SOLUBILITY |
|---|---|---|
| I | High | High |
| II | High | Low |
| III | Low | High |
| IV | Low | Low |

Examples of Class II drugs are cyclosporine, danazol, griseofulvine, ketoconazole, itraconazole, mefenamic acid and others. The enhancement of the extent of absorption, when Class II drugs are co-administered with food in general, has been documented in the literature.

It has been surprisingly found that the object of the present invention is achieved by employing milk as a solubilizing/dispersing agent in order to enhance the bioavailability of the active ingredient.

Milk is particularly useful for highly non-polar drugs because is a medium with high solubilization efficiency. The dilution of the liquid pharmaceutical compositions and the dissolution of the powdered pharmaceutical compositions prior to oral administration in milk are made by short agitation.

The main structural elements of milk are fat globules, casein micelles, globular proteins and lipoprotein particles. The size of fat globules range from 0.1 to 15 µm, the total globule number is about $15 \times 10^9$/ml which creates a fat surface area of 700 $cm^2$/ml of milk. Thus, milk is an oil-in-water emulsion and lipophilic substances can be taken up easily, because they are soluble in the fat globules. Moreover, ionized lipophilic drugs can be easily dissolved in milk due to its high aqueous content.

For the purposes of the present invention solubility studies were performed with lipophilic drugs in various buffers as well as studies dealing with effect of the added buffer volume on milk pH.

Mefenamic acid is a non-steroidal anti-inflammatory drug used to treat pain. It is known as a problematic drug in granulation, tableting, and dissolution due to its poor solubility, hydrophobicity, and tendency to stick to surfaces. It is administered in relatively high doses (500 mg) and it's most common side effect is stomach irritation. All these issues of Mefenamic acid make it an ideal drug according to the objects of the present invention.

Solubility studies were performed at 25° C. in various buffers. More specifically:
a) 0.2M $NaH_2PO_4$—NaOH at nominal pH: 6, 7, 8, 9, 10, 11, 11.2, 11.4, 11.6, 11.8, 12;
b) 0.1M $NaH_2PO_4$—NaOH at nominal pH: 11, 11.2, 11.4, 11.6, 11.8, 12; and
c) 0.2M $KH_2PO_4$—KOH at nominal pH: 6, 7, 8, 9, 10, 11, 12.

An excess quantity of mefenamic acid powder was added to a 25 ml flask containing 15 ml of the appropriate aqueous medium. The flasks were placed in a thermostated water bath at 25° C. under constant shaking rate of 100 rpm for 48 h. The filtrated samples of mefenamic acid were monitored at 285 nm. Calibration curves were performed for every buffer, prior to measurements.

The results obtained (FIG. 1) demonstrate that the solubility of mefenamic acid is greatly enhanced in a nominal pH range of 11-12 using a 0.2M $NaH_2PO_4$—NaOH buffer.

Extensive experiments regarding the solubility of various lipophilic active ingredients in different alkaline pH buffers were performed as well.

Solubility studies with Tolfenamic acid, Ketoprofen and Nimesulide have been performed and said drugs were found to have an excess solubility of 35.15, 73.04 and 52.63 mg/ml, respectively in buffer 0.2M $NaH_2PO_4$/NaOH at nominal pH=12.

Tenoxicam has been found to have increased solubility of 14.35 mg/ml in buffer 0.1M $NaH_2PO_4$/NaOH at nominal pH=12. Finally, Meloxicam in buffer glycine/NaOH at nominal pH=12 had also an increased solubility of 15.38 mg/ml.

Moreover, experiments were performed to demonstrate the effect of the added buffer volume on milk pH. These experiments were performed with three different volumes of milk i.e. 100, 150 and 200 ml using 4 different types of milk such as 3.5% fat (whole milk) long duration milk, 1.5% fat (skimmed milk) long duration milk, 3.5% fat fresh milk and 1.5% fat fresh milk.

Figure 2:
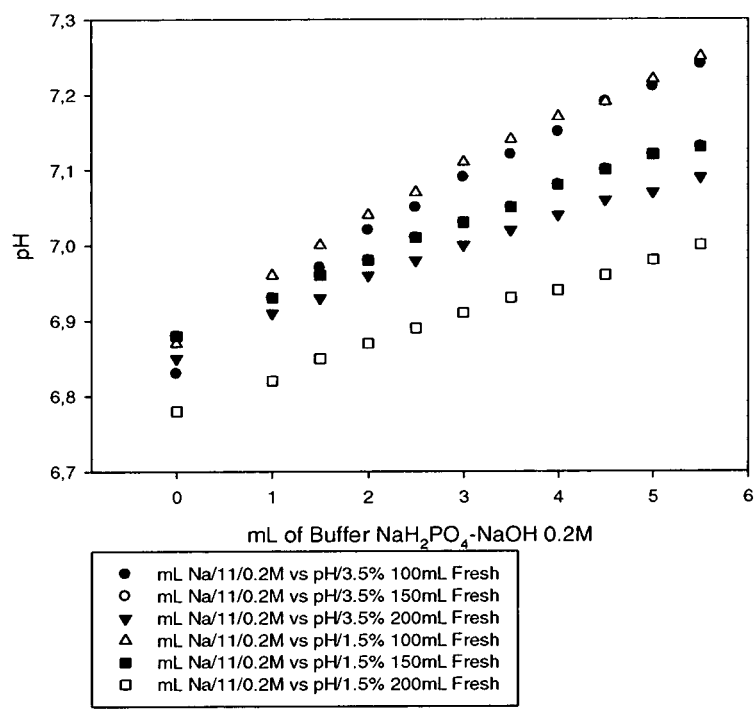
FIG. 2 shows pH variations of two different types of fresh milk by progressive addition of buffer 0.2M $NaH_2PO_4$—NaOH.

The buffers used to initially dissolve the lipophilic drug were the following:

a) 0.2M $NaH_2PO_4$—NaOH (nominal pH 11) (FIG. 2) and
b) 0.1M $NaH_2PO_4$—NaOH (nominal pH 11).

The appropriate buffer was added in milk gradually under magnetic stirring and the increase of the milk pH was measured. Initially, 1 ml buffer was added and the milk pH was measured followed by successive additions of 0.5 mL of the appropriate buffer and pH measurements until a total of 5.5 ml of the buffer were added.

The results indicate that the addition of the alkaline buffer cause a slight increase in milk pH from 0.1 to 0.3 pH units. The increase is higher and close to 0.3 pH units when the higher strength of buffer (0.2 M) and the smaller volume of 100 ml of milk were used.

Subsequently, experiments were performed in order to evaluate if an active ingredient initially dissolved in buffer, when solubilized/dispersed in milk, is suitable for oral administration. Various active agents dissolved in buffers of nominal pH=12 and then solubilized/dispersed in 150 ml 3.5% fat long duration milk were tested (Table 2). The buffer volume was increased by 0.5 ml each time and the pH values after each addition were measured.

Figure 3:
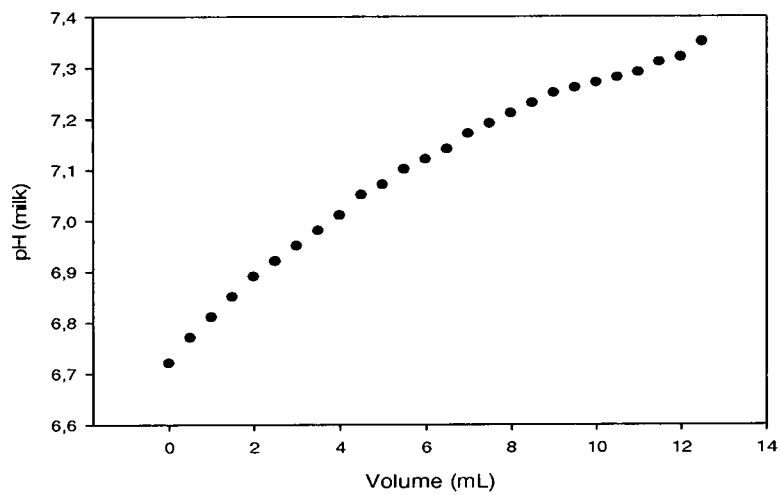
FIG. 3 shows pH variations of long duration whole milk by progressive addition of 12.5 ml of Mefenamic acid (40 mg/ml Mefenamic acid) dissolved in buffer 0.2M $NaH_2PO_4$—NaOH at nominal pH=12 according to the present invention.
Figure 4:
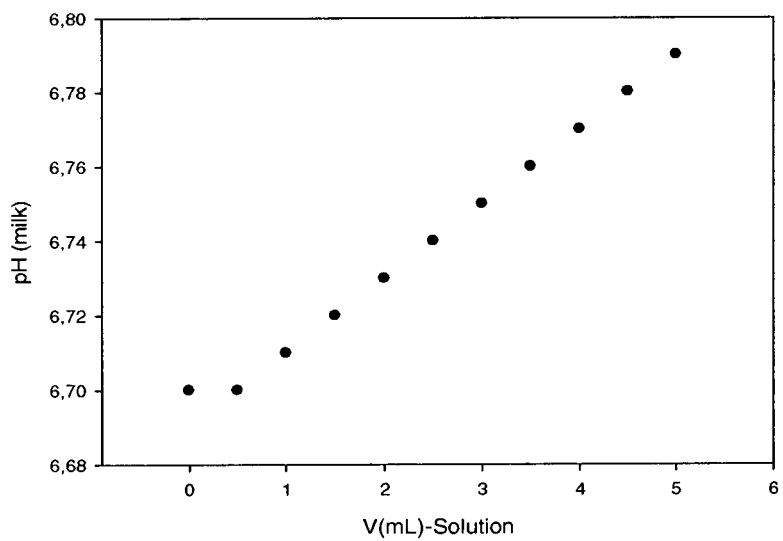
FIG. 4 shows pH variations of long duration whole milk by progressive addition of 5 ml of Meloxicam (3 mg/ml Meloxicam) dissolved in buffer 0.05M Glycine-NaOH according to the present invention.
Figure 5:
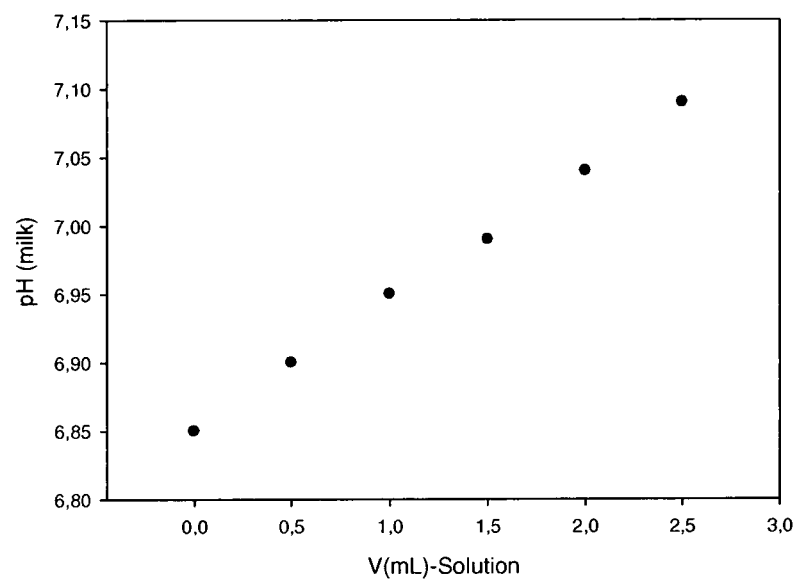
FIG. 5 shows pH variations of long duration whole milk by progressive addition of 2.5 ml of Nimesulide (40 mg/ml Nimesulide) dissolved in buffer 0.2M $NaH_2PO_4$—NaOH according to the present invention.

Surprisingly, all the results indicate that the addition of a small volume of the buffer solutions of lipophilic drugs to milk for the preparation of the final pharmaceutical composition prior to its administration will produce a minor increase in milk pH (FIGS. 3, 4, 5). Therefore, it is feasible to administrate such pharmaceutical compositions.

These results can be attributed to the high buffer capacity of milk that is able to keep the pH value of the pharmaceutical composition to a suitable range for oral administration. Due to the low viscosity of milk the liquid pharmaceutical compositions of the present invention when diluted in milk are mixed easily and even though the pH value is around 7, visual inspection of the pharmaceutical composition upon its preparation for several minutes, did not reveal any physical change or precipitation of the active ingredient.

TABLE 2

Final pH values of composition according to the present invention

| Active ingredient | Dose (mg) | Concentration (C) (mg/mL) | Solution Volume (mL) | Buffer | Final pH |
| --- | --- | --- | --- | --- | --- |
| Mefenamic acid | 500 | 40 | 12.5 | $NaH_2PO_4$/NaOH 0.2M | 7.35 |
| | 500 | 25 | 20 | $NaH_2PO_4$/NaOH 0.2M | 7.73 |
| | 50 | 10 | 5 | $NaH_2PO_4$/NaOH 0.2M | 6.81 |
| | 100 | 10 | 10 | $NaH_2PO_4$/NaOH 0.2M | 7.01 |
| Tolfenamic acid | 100 | 10 | 10 | $NaH_2PO_4$/NaOH 0.2M | 7.42 |
| | 100 | 20 | 5 | $NaH_2PO_4$/NaOH 0.2M | 7.03 |
| | 100 | 20 | 5 | $NaH_2PO_4$/NaOH 0.1M | 6.75 |
| | 200 | 20 | 10 | $NaH_2PO_4$/NaOH 0.2M | 7.34 |
| | 300 | 25 | 12 | $NaH_2PO_4$/NaOH 0.2M | 7.40 |
| Ketoprofen | 200 | 50 | 4 | $NaH_2PO_4$/NaOH 0.2M | 6.71 |
| | 100 | 50 | 2 | $NaH_2PO_4$/NaOH 0.2M | 6.72 |
| Meloxicam | 7.5 | 1.5 | 5 | Glycine/NaOH 0.05M | 6.74 |
| | 15 | 3 | 5 | Glycine/NaOH 0.05M | 6.79 |
| | 15 | 6 | 2.5 | Glycine/NaOH 0.05M | 6.73 |
| Tenoxicam | 20 | 10 | 2 | Glycine/NaOH 0.05M | 6.79 |
| Nimesulide | 100 | 40 | 2.5 | $NaH_2PO_4$/NaOH 0.2M | 7.09 |

Additionally, experiments regarding the solubility of various lipophilic active ingredients in alcoholic solutions were performed.

At 25° C. the saturation solubility of cyclosporine in a solution composed of 40% ethanol and 60% water is 4.97 mg/ml. In mixtures composed of 60% ethanol and 40% water the solubility of cyclosporine was above 60 mg/ml at all temperatures investigated (5, 25 and 37° C.). Therefore, a volume of 3 mL of a pharmaceutical composition of cyclosporine solution of 100 mg/ml in ethanol is easily diluted by gentle agitation to a volume of milk between 20 and 500 mL for the delivery of a therapeutic cyclosporine dose of 300 mg.

Figure 6:
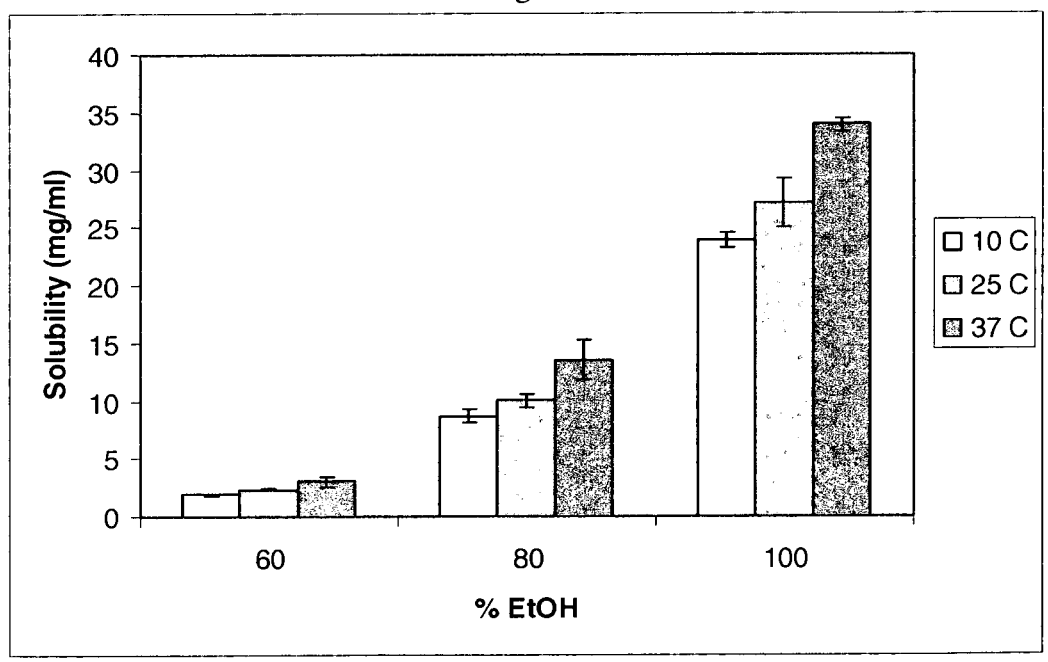
FIG. 6 shows average solubility of Danazol at three different temperatures (10, 25 and 37° C.) dissolved in ethanol: water solutions 60:40, 80:20 and 100% ethanol.

Also, the solubilities of Danazol at three different temperatures (10, 25 and 37° C.) dissolved in ethanol: water solutions 60:40, 80:20 and 100% ethanol were measured (Table 3). Solubility increases at higher temperatures and higher amounts of ethanol used (FIG. 6)

TABLE 3

Average solubility of Danazol at three different temperatures (10, 25 and 37° C.) dissolved in ethanol:water solutions 60:40, 80:20 and 100% ethanol

| | Average Solubility (mg/ml) ± standard deviation | | |
| --- | --- | --- | --- |
| % EtOH | 10° C. | 25° C. | 37° C. |
| 60 | 1.93 ± 0.08 | 2.35 ± 0.05 | 3.01 ± 0.42 |
| 80 | 8.70 ± 0.64 | 10.04 ± 0.58 | 13.54 ± 1.71 |
| 100 | 23.90 ± 0.65 | 27.15 ± 2.08 | 33.91 ± 0.54 |

The powdered pharmaceutical compositions of the present invention are dissolved easily in milk since the drug particles in either micronized form or in granulated powder form have high surface area while the lipophilic drug is soluble in the milk fat globules. This means very rapid partition equilibrium of drug between fat globules and milk plasma. Overall, the high solubilization efficiency of milk for lipophilic compounds enhances the advantages of the techniques utilized in the present invention for the increase of the solubility and/or dissolution of the drugs. Thus, the use of milk as a solubilizing agent of liquid and powdered orally administered pharmaceutical compositions of lipophilic drugs of the present invention can offer improvements in the drug's absorbability.

The pharmaceutical composition according to the present invention can be provided to a patient in a convenient way in order to facilitate its use. A suitable packaging may comprise different containers, two or three or more, each having the components of the pharmaceutical composition of the present invention, separately. A solution of active ingredient with buffer or alcoholic solution, may be in one container that can be added to the milk container and after a short agitation is ready for use or the drug may be added to the buffer or alcoholic solution first and then to milk in order to fulfill a three step process to a ready to use dosage form.

Nevertheless, one multi-compartment device can achieve better convenience and compliance by the patient. Said device contains in one compartment the amount of milk needed and in another compartment the solution/dispersion of the active ingredient in the buffer or alcoholic solution. The two compartments can be designed in such a way that are separated one from the other with an easy to break membrane so that the drug solution can be added to milk and after a short agitation to be administered to the patient.

It is obvious that the device, as described above, might have three or more compartments each of them comprising one of the three constituents according to the present invention.

Various modifications to the separate container packaging and the multi compartment device, as described above, are applicable as well. Also, the constituents of the present invention can be in various forms. For example milk can be in freeze dried form so that it can be reconstituted in water or the active substance can be in the form of an effervescent tablet.

Moreover, according to another embodiment of the present invention, besides the administration with the use of a proper device, it is possible to add a certain volume of the active ingredient-solubilizing agent solvent in milk during its manufacturing process. The pharmaceutical composition would be in one container and the patient could drink a certain volume of the packaged drug-milk solution which corresponds to the therapeutic dose and the rest of the composition could be kept in the refrigerator for further use according to the dosage regimen design of the drug and its shelf life.

The pharmaceutical composition of the present invention might also comprise solubilization of the lipophilic drug with one or more surfactants such as cremophor EL, Tween 80, sodium lauryl sulfate, cetyl trimethyl ammonium bromide, with one or more complexing agents such as hydroxypropyl-β-cyclodextrin, sulfobutylether-β-cyclodextrin and nicotinamide or one or more oil/lipid such as oleic acid, vitamin E TPGS, Gelurite 44/14. All the solubilization agents mentioned above, as well as those described in the present invention, may also be used in combinations of two or more in order to achieve the dissolution of said compounds. Further, the pharmaceutical composition of the present invention can comprise additional pharmaceutically acceptable excipients that will not alter its properties such as taste masking agents.

It is also an object of the present invention to provide pharmaceutical compositions of NSAIDs, which upon dilution in milk and administration help prevent stomach irritation. It is well known and recommended to drink milk after administration of an active ingredient that causes stomach irritation.

The following examples, without limiting the scope or spirit of the invention, illustrates that by using a device as described above, it is feasible to provide a pharmaceutical composition that enhances the compliance of the patient and reduces the side effect of stomach irritation.

EXAMPLES

Example 1

Acetylsalicylic acid (ASA) is widely used as an analgesic, anti-inflammatory and antipyretic drug. In addition, low-dose ASA is employed as an antithrombotic agent. ASA is rapidly hydrolyzed in vivo to salicylic acid (SA) which is also active.

SA is further metabolized by hydroxylation to gentisic acid (GA), and by conjugation to salicyluric acid (SUA) and other conjugates.

Initially, in vitro solubility studies were performed in water, 0% fat fresh milk, 1.5% long duration milk, 1.5% fat fresh milk and 1.5% fat fresh milk having 70% less lactose in 10° C. and 25° C. The results indicated no significant difference in solubility of ASA between the various solubilizing mediums even after 24 or 48 hours.

Subsequently, a comparative bioavailability study of an effervescent 500 mg aspirin tablet administered with water and an equivalent dose of aspirin powder dissolved/dispersed in milk, with the use of a device as described in the current application, were evaluated. The first formulation (Reference, R) is a solution of acetylsalicylic acid in water after the addition of an effervescent tablet containing 500 mg of active substance in 200 ml of water. The second formulation according to the present invention (Test, T) is prepared by dissolving the active substance in 20 ml of water and then added to 180 mL of milk by utilizing a proper device as described before.

A replicate, 4-period study design was used with 2 healthy male volunteers (eight administrations in total). Blood samples were collected in selected time intervals and analyzed by using a chromatographic technique. Blood samples were collected in predefined time intervals.

Figure 7:
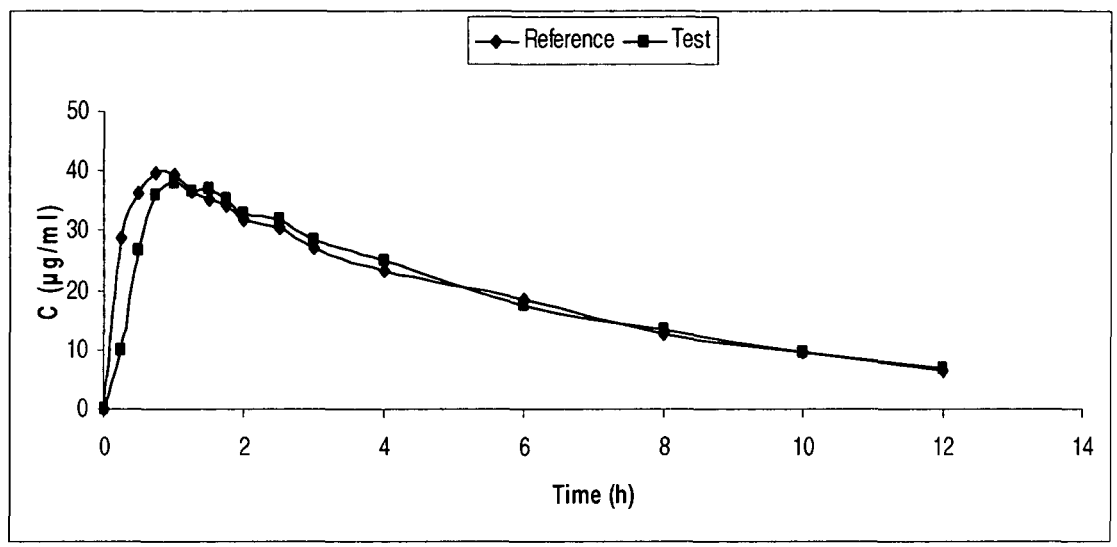
FIG. 7 shows average plasma values of salicylic acid for the reference composition and test composition according to the present invention.

The table below indicates that the two formulations exhibit similar in vivo results therefore it is obvious that according to the invention as disclosed herein, it is feasible to provide a pharmaceutical composition of milk with an active agent utilizing a proper device and accordingly provide inhibition of stomach irritation to the patient (FIG. 7).

TABLE 4

Pharmacokinetic results of test composition versus reference product

| | $AUC_{0 \to t}$ (µg * h/ml) | $AUC_{0 \to \infty}$ (µg * h/ml) | $C_{max}$ (µg/ml) | $t_{max}$ (h) |
|---|---|---|---|---|
| R1 Subject 1 | 251.88 | 292.35 | 41.38 | 1.00 |
| R1 Subject 2 | 218.27 | 240.29 | 41.61 | 0.75 |
| R2 Subject 1 | 259.85 | 337.79 | 39.54 | 0.75 |
| R2 Subject 2 | 202.76 | 225.54 | 39.22 | 1.00 |
| T1 Subject 1 | 285.24 | 359.41 | 47.67 | 0.75 |
| T1 Subject 2 | 201.22 | 214.94 | 36.88 | 1.25 |
| T2 Subject 1 | 246.46 | 307.84 | 39.35 | 1.00 |
| T2 Subject 2 | 186.98 | 210.53 | 33.58 | 1.50 | wherein:

C max = (peak concentration) is the highest concentration reached by the drug in plasma after dosing;

T max = time of Cmax $AUC_{0-t}$ = (area under the curve) is the total area under the time-plasma concentration curve, from time 0 to the last measurable concentration, as calculated by the linear trapezoidal method; it represents a measure of the bioavailability of the drug.

$AUC_{0 \to \infty}$ = (area under the curve) is the total area under the time-plasma concentration curve from time 0 to infinity.

These data show that the properties of the two formulations are comparable with respect to the main pharmacokinetic parameters.

Example 2

Meloxicam is an NSAID of the oxicam class that exhibits anti inflammatory, analgesic and antipyretic activities. It is available as a tablet of 7.5 mg and 15 mg and as an oral suspension (7.5 mg/5 ml).

The bioavailability and pharmacokinetic profile of Meloxicam in a pharmaceutical composition according to the present invention was determined in an "in vivo" single-dose study.

The single-dose study was conducted in one healthy volunteer using the following formulation: 15 mg of Meloxicam powder were dissolved in 2.5 ml of 0.05M Glycine-NaOH buffer solution (nominal pH=12). The solution was added in 150 ml of 3.5% fat milk, agitated and administered.

The reference composition was a 15 mg Meloxicam tablet (Mobic® 15 mg).

Figure 8:
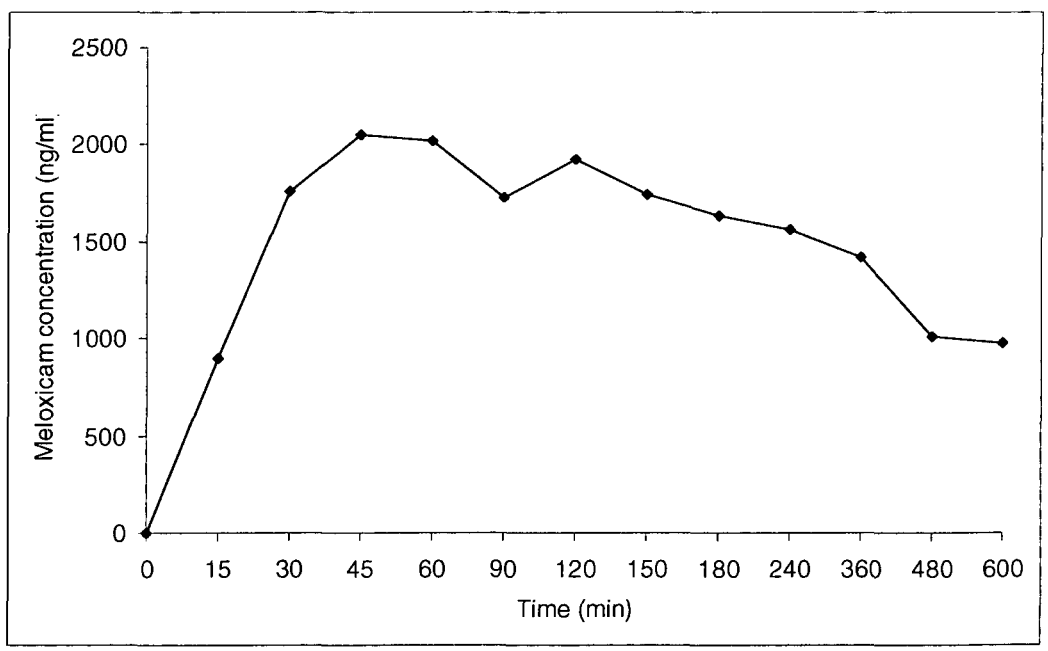
FIG. 8 shows plasma values of Meloxicam versus time of a composition according to the present invention.

The volunteer was maintained in the fasting state for 6 h after administration, after an overnight fast. Blood samples (5 ml) were taken at different times such as at 15, 30, 45, 60, 90, 120, 150 min and at 3, 4, 6, 8, 10, 12, 24, 48 and 72 h after administration. The blood samples were analyzed and the plasma concentration of Meloxicam was determined (FIG. 8).

Table 5 shows the main pharmacokinetic parameters obtained from the test.

TABLE 5

Pharmacokinetic results of the pharmaceutical composition of example 2

| Pharmacokinetic parameter | Results |
|---|---|
| $AUC_{0 \to 72}$ (ng h/ml) | 35313.33 |
| $AUC_{0 \to \infty}$ (ng h/ml) | 37150.12 |
| $C_{max}$ (ng/ml) | 2047.282 |
| $T_{max}$ (min) | 45 |
| $t_{1/2}$ (h) | 16.5 |

According to the oral bioavailability of 15 mg Meloxicam (Mobic®) composition under fasted conditions, $T_{max}$ is being achieved at four or more hours after administration and $C_{max}$ is substantially lower than that obtained by the current composition.

Therefore, the composition of Meloxicam according to the present invention provides much faster release from any symptom and more efficient pharmacological action can be obtained.

TABLE 6

Average Meloxicam concentration of samples taken from the surface, middle and bottom of a glass containing the composition of example 2.

| | Average Meloxicam Concentration (µg/ml) ± SD | | |
|---|---|---|---|
| Time (min) | Surface | Middle | Bottom |
| 2 | 104.95 ± 5.80 | 103.57 ± 5.28 | 106.26 ± 3.29 |
| 60 | 106.00 ± 2.69 | 106.63 ± 1.96 | 108.49 ± 1.60 |
| 120 | 106.35 ± 0.66 | 108.28 ± 3.41 | 108.93 ± 0.45 |
| 240 | 108.68 ± 0.53 | 109.11 ± 0.68 | 111.60 ± 0.29 |

In addition, the composition of example 2 was tested for the uniformity of the distribution of Meloxicam in the formulation. In order to measure the drug concentration, samples were taken from the surface, middle and bottom of a glass containing the composition at 2, 60, 120 and 240 minutes after its preparation. The experiment was run in triplicate at room temperature and the results, as shown in Table 6, indicate that a uniform concentration is obtained in the whole volume of the composition.

Example 3

Cyclosporine is an immunosuppressant drug widely used in post-allogeneic organ transplant. It is also used in psoriasis, severe atopic dermatitis and infrequently in rheumatoid arthritis and related diseases, although it is only used in severe cases. It has been investigated for use in many other autoimmune disorders. Cyclosporine A, the main form of the drug, is a cyclic non ribosomal peptide of 11 amino acids.

The bioavailability and pharmacokinetic profile of Cyclosporine A in a pharmaceutical composition according to the present invention was determined in an "in vivo" single-dose study.

Prior to the "in vivo" study the solubility of Cyclosporine A in ethanolic solutions was investigated. Cyclosporine A has been proved to have very high solubility in ethanol: water 60:40 solutions in a wide range of temperatures (5 to 37° C.). More specifically Cyclosporine A had solubility above 60 mg/ml in all temperatures, which means that 5 ml of the solution can dissolve a dose of 300 mg active substance.

The single-dose study was conducted in one healthy volunteer using the following formulation: 100 mg of Cyclosporine A powder were dissolved in 5 ml of ethanol: water 60:40 solution (20 mg/ml). The solution was added in 200 ml of 3.5% fat milk, agitated and administered.

The reference composition was a 100 mg Neoral® tablet.

Figure 9:
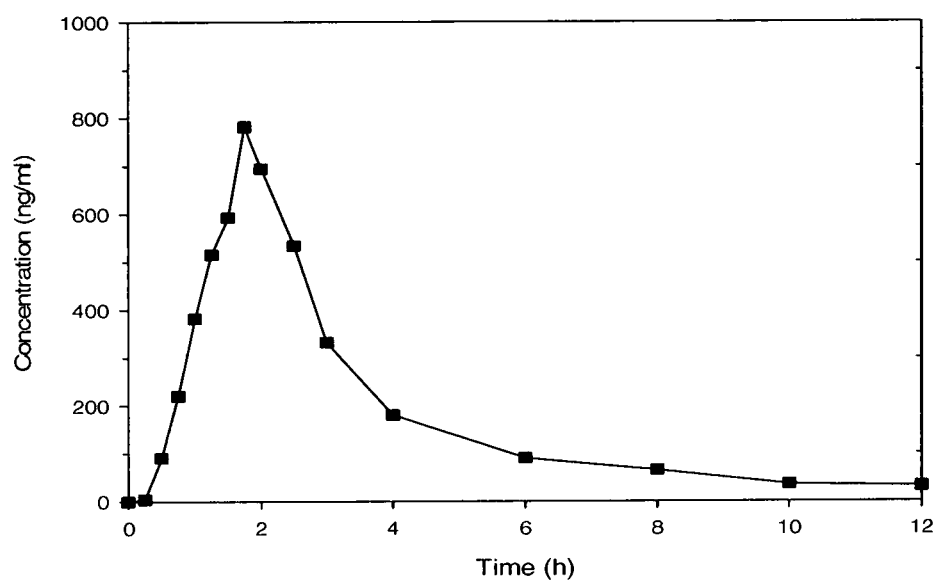
FIG. 9 shows plasma values of Cyclosporine A versus time of a composition according to the present invention.

The volunteer was maintained in the fasting state for 4 hours after administration and no smoking, alcoholic, caffeine containing beverages or juices were allowed during the test. Blood samples were taken at different times such as at 0.25, 0.50, 0.75, 1.25, 1.50, 1.75, 2.00, 2.50, 3.00, 4.00, 6.00, 8.00, 10.00 and 12.00 h after administration. The blood samples were analyzed and the plasma concentration of Cyclosporine A was determined (FIG. 9).

Table 7 shows the main pharmacokinetic parameters obtained from the test.

TABLE 7

Pharmacokinetic results of the pharmaceutical composition of example 3

| Pharmacokinetic parameter | Results |
|---|---|
| $AUC_{0 \to 12}$ (mg h/lt) | 2.107 |
| $AUC_{0 \to \infty}$ (mg h/lt) | 2.279 |
| $C_{max}$ (ng/ml) | 782.3 |
| $T_{max}$ (h) | 1.75 |
| $t_{1/2}$ (h) | 3.81 |

The results obtained from the test composition were compared with currently available 100 mg compositions of Cyclosporine A such as Neoral®.

The oral bioavailability of 100 mg Cyclosporine A according to the present invention exhibit increased $C_{max}$ and $AUC_{0 \to \infty}$ values compared to Neoral® composition while the $T_{max}$ remained the same.

Therefore, the composition of Cyclosporine A according to the present invention may provide a pharmaceutical composition with the same effect resulting in better patient compliance and less side effects than any available reference product.

Example 4

The physicochemical properties of milk-drug formulations according to the present invention have been investigated. In particular, the size distribution of casein micelles and fat globules, the ζ-potential, the conductivity and the polydispersity index were measured by using dynamic light scattering (DLS).

Long life milk (UHT) of 3.6% fat and Mefenamic acid, Tolfenamic acid, Ketoprofen, Meloxicam, Tenoxicam and Nimesulide were used as model ionized compounds.

The physicochemical characteristics of drug free solutions of i) 0.1M $NaH_2PO_4$—NaOH (pH: 8, 10, 12), ii) 0.2M $NaH_2PO_4$—NaOH (pH: 8, 10, 12), iii) 0.05M glycine-NaOH (pH: 8, 10, 12), and iv) 0.1M glycine-NaOH (pH: 8, 10, 12) in milk were initially studied.

However, there was no clear tendency between the values by varying either the pH or the ionic strength, respectively.

Subsequently, specific amounts of the ionized nonsteroidal anti-inflammatory drugs were weighed and dissolved in the following aqueous buffers: i) 0.2M $NaH_2PO_4$—NaOH (pH 12), and ii 0.05M glycine-NaOH (pH 12). The drug containing buffer solutions were added in 15 mL of 3.6% UHT milk and the size distribution of the fat globules and micelles were measured accordingly. The surface charge of the produced emulsions was further investigated by measuring their ζ-potential and their conductivity. Table 8 below presents the obtained results.

TABLE 8

The values of size of proteins-lipoproteins (Pk1), fat globules (Pk2), the ζ-average, volume mean, polydispersity index (P.I). and ζ-potential of the final NSAIDs-buffer/milk formulations

| NSAIDs-buffer/<br>milk formulation | Pk1(nm)<br>± SD | Pk2(nm)<br>± SD | Z-Avg<br>(d.nm)<br>± SD | Vol.Mean<br>(d.nm)<br>± SD | PI<br>± SD | Z-Potential<br>(mV) ± SD |
|---|---|---|---|---|---|---|
| Milk 3.6% fat | 55.9 (2.6) | 805.267 (20.08) | 265.1 (4.9) | 657.9 (18.7) | 0.468 (0.022) | −34.2 (0.4) |
| Mefenamic acid: 500 mg in 12.5 mL 0.2M $NaH_2PO_4$—NaOH pH 12 | 63.66 (9.311) | 974.366 (8.96) | 364.6 (16.108) | 930633 (54.6) | 0.449 (0.005) | −38 (1.3) |
| Mefenamic acid: 100 mg in 10 mL 0.2M $NaH_2PO_4$—NaOH pH 12 | 43.993 (16.67) | 940.3667 (45.84) | 279267 (15.85) | 704233 (32.55) | 0.464 (0.012) | −31.1 (4.744) |
| Mefenamic acid: 50 mg in 5 mL 0.2M $NaH_2PO_4$—NaOH pH 12 | 48.883 (18.398) | 927.6 (27.58) | 314.34 (16.23) | 857.7 (15.47) | 0.459 (0.012) | −30.1 (2.155) |
| Tolfenamic acid: 100 mg in 10 mL 0.2M $NaH_2PO_4$—NaOH pH 12 | 51.67 (18.6) | 861.6 (22.874) | 269.27 (18.75) | 691.94 (84.69) | 0.445 (0.013) | −34.2 (1.1) |
| Tolfenamic acid: 200 mg in 10 mL 0.2M $NaH_2PO_4$-NaOH pH 12 | 48.997 (7.779) | 973.1 (53.63) | 322.1 (4.66) | 880.7 (84.69) | 0.473 (0.014) | −35.3 (1.58) |
| Tolfenamic acid: 300 mg in 12 mL 0.2M $NaH_2PO_4$-NaOH pH 12 | 70.51 (17.68) | 947.67 (21.57) | 368 (16.86) | 920.74 (76.72) | 0.45 (0.01) | −35.43 (1.285) |
| Ketoprofen: 100 mg in 2 mL 0.2M $NaH_2PO_4$—NaOH pH 12 | 51.31 (17.35) | 868 (70.6) | 266.24 (17.35) | 688.74 (78.9) | 0.46 (0.003) | −35.03 (1.22) |
| Ketoprofen: 200 mg in 4 mL 0.2M $NaH_2PO_4$—NaOH pH 12 | 47.74 (7.28) | 800.23 (59.6) | 257.1 (10.42) | 611 (65.93) | 0.46 (0.012) | −34.43 (2.42) |
| Nimesulide: 100 mg in 2.5 mL 0.2M $NaH_2PO_4$—NaOH pH 12 | 39.57 (8.1) | 821.1 (75.64) | 260 (21.81) | 605.16 (48.63) | 0.446 (0.02) | −39.57 (8.1) |
| Meloxicam: 15 mg in 2.5 mL 0.05M glycine-NaOH pH 12 | 61.1 (5.76) | 736.43 (61.03) | 226.37 (5.63) | 433.1 (16.64) | 0.43 (0.002) | −34.2 (1.21) |
| Meloxicam: 7.5 mg in 5 mL 0.05M glycine-NaOH pH 12 | 52.95 (6.3) | 828.8 (45.71) | 250.36 (15.44) | 561.83 (26.89) | 0.447 (0.006) | −33.9 (0.85) |
| Tenoxicam: 20 mg in 2 mL 0.05M glycine-NaOH pH 12 | 67.67 (19.1) | 871.76 (98.2) | 266 (21.3) | 622.9 (63.93) | 0.457 (0.004) | −33.23 (1.15) |

The size of the fat globules of 3.6% fat UHT milk (used as reference) was 805.267±20.08 nm and the size of the proteins-lipoproteins was 55.9±2.6 nm. The size of both constituents i.e. fat globules and proteins-lipoproteins of the milk was slightly increased after the addition of incrementing volumes (μL) of 0.2 M $NaH_2PO_4$—NaOH buffer solution, while the increase after the addition of 0.05 M glycine-NaOH buffer solutions at various pH was negligible.

The addition of alkaline buffer solutions caused a slight change to the initial ζ-potential value of 3.6% fat UHT milk (−34.2±1.2 mV). All drug-free buffer/milk formulations exhibited values ranging from −32.8±0.8 to −38.8±1.25 mV.

The size of the fat globules slightly increased after the addition of the i) NSAIDs-phosphate buffer/milk formulations, while in ii) NSAIDs-glycine buffer/milk formulations the changes were negligible. There was no clear trend between the values by varying either the pH or the ionic strength, respectively. The results of the size of the milk proteins-lipoproteins follow the same pattern.

The ζ-potential values of the NSAIDs-buffer/milk formulations ranged from −33±1.2 to −35.9±1.8 mV, exhibiting negligible change compared to the initial ζ-potential value of milk.

Example 5

Ketoprofen, meloxicam and nimesulide were used for the stability studies that were performed. The drugs were dissolved in the following buffers: 0.2 M NaH$_2$PO$_4$—NaOH pH 12 and 0.05 M glycine-NaOH pH 12.

A weighted amount of drug, corresponding to its therapeutic dose, was dissolved in the appropriate volume of alkaline buffer. The solutions, filled into glass vials, sealed and long term (25° C.±2° C., 60% RH±5%), intermediate (30° C.±2° C., 65% RH±5%) and accelerated (40° C.±2° C., 75% RH±5% RH) stability studies were conducted. Also, the pH values of the aqueous alkaline NSAIDs solutions were measured before storage and at the predetermined time points.

No discoloration or precipitation observed at all samples during the stability studies. For ketoprofen, the total amount of drug for the long term studies at 25° C. (3, 6 and 9 months) ranged from 101-105% compared to the initial value. At the accelerated stability studies the total amount ranged from 99.9-106% and 99.7-105.5% for 30° C. and 40° C. compared to the initial value, respectively.

For nimesulide the total amount of drug for the long term studies at 25° C. (3 and 6 months) ranged from 96.5-107%, while at the accelerated stability studies ranged from 99.7-100.2% and 101-118% for 30° C. and 40° C., respectively, compared to the initial value.

For meloxicam, for the long term studies at 25° C. (3, 6 and 9 months) the concentration ranged from 99 to 103%, while at the accelerated stability studies ranged from 96-103% for both 30° C. and 40° C., compared to the initial value.

With respect to pH values, for ketoprofen, the change of pH ranged between 100.6-102% for both long term and accelerated studies, for all three temperatures, while for nimesulide ranged between 98.8-100.2%. pH values of meloxicam's solutions, for the long term studies at 25° C. (3, 6 and 9 months) ranged from 100.9-102% compared to the initial value. At the accelerated stability studies the final pH ranged from 100.5-102% and 100.6-101.6% for 30° C. and 40° C. compared to the initial value.

For both, long term and accelerated stability studies the % change of drug amount for ketoprofen, nimesulide and meloxicam was within acceptable ranges. The % pH change, for all three compounds was negligible.

Consequently, it has been found that the compositions according to the present invention are stable and have acceptable physicochemical properties and can be considered, with respect to the pharmacological performance, the best bioavailable formulations currently available in comparison with the marketed reference products.

This fact gives the possibility to manufacture a pharmaceutical composition for human and veterinary use with the same effect resulting in better patient compliance and less side effects than the reference product.

While the present invention has been described with respect to the particular embodiments, it will be apparent to those skilled in the art that various changes and modifications may be made in the invention without departing from the spirit and scope thereof, as defined in the appended claims.

The invention claimed is:

1. A pharmaceutical composition for oral administration comprising:
a therapeutically effective quantity of insoluble or practically insoluble in water lipophilic active ingredient or a pharmaceutically acceptable salt thereof; wherein the lipophilic active ingredient comprises a non-steroidal anti-inflammatory drug or a pharmaceutically acceptable salt thereof;
an effective amount of milk as a solubilizing/dispersing agent to enhance bioavailability and/or improve solubility; and
an alkaline buffer with a nominal pH value from 11 to 12 which is selected from the group consisting of NaH$_2$PO$_4$/NaOH 0.2M, NaH$_2$PO$_4$/NaOH 0.01M, KH$_2$PO$_4$/KOH 0.2M and Glycine/NaOH 0.05M;
wherein a solution of said active ingredient with said alkaline buffer with a nominal pH value from 11 to 12 is formed and an appropriate volume of said solution containing the therapeutic dose of the active ingredient is dispersed in a volume of milk between 20 and 500 mL and subsequently is gently agitated prior to oral administration.

2. The pharmaceutical composition according to claim 1, wherein the composition further comprises at least one co-solvent, wherein said co-solvent comprises at least one of ethanol, propylene glycol, polyethylene glycol 400, Labrasol® or mixtures thereof.

3. The pharmaceutical composition according to claim 1, wherein the composition further comprises at least one surfactant, wherein said surfactant comprises at least one of Cremophor EL®, Tween 80®, sodium lauryl sulfate, cetyl trimethyl ammonium bromide or mixtures thereof.

4. The pharmaceutical composition according to claim 1, wherein the composition further comprises at least one complexing agent, wherein said complexing agent comprises at least one of hydroxypropyl-β-cyclodextrin, sulfobutylether-β-cyclodextrin and nicotinamide or mixtures thereof.

5. The pharmaceutical composition according to claim 1, wherein the composition further comprises at least one lipid-based system, wherein said lipid-based system comprises at least one of oleic acid, vitamin E TPGS or mixtures thereof.

6. The pharmaceutical composition according to claim 1, wherein the non-steroidal anti-inflammatory drug comprises mefenamic acid, meloxicam, nimesulfide, ketoproren, tolfenamic acid, tenoxicam or pharmaceutically acceptable salts thereof.

7. The pharmaceutical composition according to claim 1, wherein said milk comprises one of whole milk, sterilized whole milk, homogenized whole milk, skim milk, reconstituted powdered whole milk, reconstituted powdered skim milk, or lactose free milk.

8. The pharmaceutical composition according to claim 1, wherein said lipophilic active ingredient is in a powder form untreated or granulated powder that has been micronized, freeze-dried or spray dried.

9. A process for the preparation of a pharmaceutical composition according to claim 1 comprising:
providing a therapeutically effective quantity of insoluble or practically insoluble in water lipophilic active ingredient or a pharmaceutically acceptable salt thereof; wherein the lipophilic active ingredient comprises a non-steroidal anti-inflammatory drug or a pharmaceutically acceptable salt thereof;
providing an effective amount of milk as a solubilizing/dispersing agent to enhance bioavailability and/or improve solubility;
forming a solution of the total quantity of said active ingredient with a buffer solution;
dispersing the formed solution in a volume of milk between 20 and 500 mL; and
subsequently gently agitating prior to oral administration.

10. The process according to claim 9, wherein the active ingredient is solubilized by using a co-solvent and/or a surfactant and/or a complexing agent and/or a lipid based system.

11. A process for the preparation of a pharmaceutical composition according to claim 1 comprising:
   providing a therapeutically effective quantity of insoluble or practically insoluble in water lipophilic active ingredient or a pharmaceutically acceptable salt thereof; wherein the lipophilic active ingredient comprises a non-steroidal anti-inflammatory drug or a pharmaceutically acceptable salt thereof; wherein the active ingredient is in powder form;
   providing an effective amount of powdered milk corresponding to a volume of milk between 20 and 500 mL as a solubilizing/dispersing agent to enhance bioavailability and/or improve solubility;
   adding the total quantity of said active ingredient in powder form into the total quantity of the powder milk to an appropriate container, thereby forming a powdered mixture; packaging said powdered mixture; and
   reconstituting said powdered mixture with a water volume between 20 and 500 ml and an alkaline buffer with a nominal pH value from 11 to 12 which is selected from the group consisting of $NaH_2PO_4/NaOH$ 0.2M, $NaH_2PO_4/NaOH$ 0.01 M, $KH_2PO_4/KOH$ 0.2M and Glycine/NaOH 0.05M, prior to oral administration.

12. The pharmaceutical composition according to claim 1, which optionally comprises pharmaceutically acceptable excipients.

13. A pharmaceutical composition for oral administration comprising:
   a therapeutically effective quantity of insoluble or practically insoluble in water lipophilic active ingredients or a pharmaceutically acceptable salt thereof; wherein the lipophilic active ingredient comprises cyclosporine;
   an effective amount of milk as a solubilizing/dispersing agent to enhance bioavailability and/or improve solubility; and
   an ethanolic solution;
wherein a solution of said active ingredient with said ethanolic solution is formed and an appropriate volume of said solution containing the therapeutic dose of the active ingredient is dispersed to a volume of milk between 20 and 500 mL and subsequently is gently agitated prior to oral administration.

* * * * *